(12) United States Patent
An

(10) Patent No.: US 11,304,449 B2
(45) Date of Patent: Apr. 19, 2022

(54) LIGHT-EMITTING ELEMENT AND AEROSOL GENERATION DEVICE COMPRISING SAME

(71) Applicant: KT&G CORPORATION, Daejeon (KR)

(72) Inventor: Hwi Kyeong An, Seoul (KR)

(73) Assignee: KT&G CORPORATION, Daejeon (KR)

( * ) Notice: Subject to any disclaimer, the term of this patent is extended or adjusted under 35 U.S.C. 154(b) by 0 days.

(21) Appl. No.: 16/764,091

(22) PCT Filed: May 9, 2019

(86) PCT No.: PCT/KR2019/005527
§ 371 (c)(1),
(2) Date: May 14, 2020

(87) PCT Pub. No.: WO2020/040401
PCT Pub. Date: Feb. 27, 2020

(65) Prior Publication Data
US 2020/0352232 A1    Nov. 12, 2020

(30) Foreign Application Priority Data
Aug. 24, 2018  (KR) .......................... 10-2018-0099426

(51) Int. Cl.
*H01L 33/48*         (2010.01)
*A24F 40/40*         (2020.01)
(Continued)

(52) U.S. Cl.
CPC ......... *A24F 40/40* (2020.01); *A61M 15/0001* (2014.02); *A61M 15/06* (2013.01);
(Continued)

(58) Field of Classification Search
CPC ... A24F 40/40; A61M 15/0001; A61M 15/06; A61M 2205/587; A61M 2205/8206; F21V 31/005; F21V 33/008
See application file for complete search history.

(56) References Cited

U.S. PATENT DOCUMENTS 6,871,982 B2    3/2005  Holman et al.
9,318,357 B2    4/2016  Brandl et al.
(Continued)

FOREIGN PATENT DOCUMENTS

EP    1995834 A1    11/2008
JP    S63-155654 U  10/1988
(Continued)

OTHER PUBLICATIONS

Office Action dated Aug. 24, 2018 in Korean Application No. 10-2018-0099426.
(Continued)

*Primary Examiner* — Fatima N Farokhrooz
(74) *Attorney, Agent, or Firm* — Sughrue Mion, PLLC

(57) ABSTRACT

A light emitting element according to an embodiment includes: a light emitting portion mounted on a PCB and configured to emit light; a light shield portion spaced from the PCB and having an opening that is formed at a location corresponding to the light emitting portion and passes light emitted from the light emitting portion; a sealing portion positioned between the light shield portion and the PCB and configured to prevent light emitted from the light emitting portion from leaking between the light shield portion and the PCB; and a transmission portion contacting one surface of the light shield portion and configured to transmit light, the one surface facing a direction away from the light emitting portion, wherein the opening has an inclined surface that is an outer circumferential surface located at one end of the opening in the direction away from the light emitting portion (Continued)

and widened in the direction away from the light emitting portion such that spread of light that passed through the opening is prevented.

13 Claims, 8 Drawing Sheets

(51) Int. Cl.
    *A61M 15/00* (2006.01)
    *A61M 15/06* (2006.01)
    *F21V 31/00* (2006.01)
    *F21V 33/00* (2006.01)
    *H01L 33/50* (2010.01)
(52) U.S. Cl.
    CPC .......... *F21V 31/005* (2013.01); *F21V 33/008* (2013.01); *H01L 33/48* (2013.01); *H01L 33/507* (2013.01); *A61M 2205/587* (2013.01); *A61M 2205/8206* (2013.01)

(56) References Cited

U.S. PATENT DOCUMENTS

| 10,193,294 | B2* | 1/2019 | Morizumi ................. H01S 3/05 |
| 10,355,183 | B2 | 7/2019 | Iwaki |
| 10,514,135 | B2* | 12/2019 | Shibata ................... F21V 7/041 |
| 11,112,069 | B2* | 9/2021 | Kozuru ............... H01S 5/02325 |
| 2006/0027828 | A1 | 2/2006 | Kikuchi |
| 2008/0116473 | A1* | 5/2008 | Sugiyama ............. H01L 33/483 257/98 |
| 2009/0003400 | A1* | 1/2009 | Nagahama ........... H01L 33/483 372/50.23 |
| 2010/0084673 | A1* | 4/2010 | Ho .......................... H01L 33/62 257/98 |
| 2012/0161180 | A1 | 6/2012 | Komatsu et al. |
| 2013/0042865 | A1 | 2/2013 | Monsees et al. |
| 2014/0070411 | A1* | 3/2014 | Okada ............... H01L 23/49811 257/737 |
| 2015/0084072 | A1 | 3/2015 | Huang et al. |
| 2015/0194572 | A1 | 7/2015 | Kwon et al. |
| 2015/0328415 | A1 | 11/2015 | Minskoff et al. |
| 2016/0131350 | A1* | 5/2016 | Li .......................... H01L 33/62 362/294 |
| 2016/0262453 | A1* | 9/2016 | Ampolini ................ A24F 40/60 |
| 2017/0309792 | A1* | 10/2017 | Tischler ................ H01L 25/165 |
| 2017/0336035 | A1 | 11/2017 | Lin et al. |
| 2017/0370555 | A1 | 12/2017 | Kim et al. |

FOREIGN PATENT DOCUMENTS

| JP | 4120984 U | 10/1992 |
| JP | H6-54081 U | 7/1994 |
| JP | 2005159082 A | 6/2005 |
| JP | 2005243738 A | 9/2005 |
| JP | 2006520518 A | 9/2006 |
| JP | 2007-329444 A | 12/2007 |
| JP | 2009218512 A | 9/2009 |
| JP | 2009224349 A | 10/2009 |
| JP | 2012142426 A | 7/2012 |
| JP | 201562226 A | 4/2015 |
| JP | 2015532541 A | 11/2015 |
| JP | 2015215429 A | 12/2015 |
| JP | 2016139734 A | 8/2016 |
| JP | 2017-59818 A | 3/2017 |
| JP | 2017-147406 A | 8/2017 |
| KR | 10-2006-0049072 A | 5/2006 |
| KR | 10-1361951 B1 | 2/2014 |
| KR | 10-2014-0049690 A | 4/2014 |
| KR | 10-2015-0081089 A | 7/2015 |
| KR | 10-2018-0000174 A | 1/2018 |
| WO | 2007/105647 A1 | 9/2007 |

OTHER PUBLICATIONS

International Search Report for PCT/KR2019/005527 dated Aug. 27, 2019 [PCT/ISA/210].
Communication dated Jun. 17, 2021, from the European Patent Office in application No. 19851975.3.
Communication dated Jun. 1, 2021, from the Japanese Patent Office in application No. 2020-527112.
Notice of Reasons for Refusal issued in the Japanese Patent Office in corresponding Japanese Patent Application No. 2020-527112 dated Feb. 21, 2022.

* cited by examiner

LIGHT-EMITTING ELEMENT AND AEROSOL GENERATION DEVICE COMPRISING SAME

CROSS REFERENCE TO RELATED APPLICATIONS

This application is a National Stage of International Application No. PCT/KR2019/005527 filed May 9, 2019, claiming priority based on Korean Patent Application No. 10-2018-0099426 filed Aug. 24, 2018.

TECHNICAL FIELD

Embodiments relate to a light emitting element and an aerosol generating device including the same, and more particularly, to a light emitting element having a structure for preventing light spread and an aerosol generating device including the light emitting element.

BACKGROUND ART

Recently, the use of electronic devices including light emitting elements is expanding. Particularly, demands for light emitting elements including light emitting diodes (LEDs) are increasing. The reason is because LEDs have long lifecycles compared to other light sources, have low power consumption, and also can be miniaturized.

A light emitting module including a plurality of light emitting elements described above may be employed in various kinds of electronic devices, as well as lighting equipment. However, typical light emitting elements attached to electronic devices, etc. have a problem of light spread due to their internal structures.

When light spread occurs in a light emitting element due to its internal structure, light quantity may be reduced and a visual effect that the light emitting element can represent may deteriorate.

To overcome this problem, a light emitting element structure capable of minimizing light spread is needed. More specifically, structural technology for preventing deterioration of a visual effect according to a reduction of light quality caused by refraction of light by applying a structure capable of changing a refraction angle of light to concentrate the light to a light emitting element is needed.

DESCRIPTION OF EMBODIMENTS

Technical Problem

Embodiments provide a light emitting element having a structure for preventing light spread.

Also, embodiments provide a light emitting module including a plurality of light emitting elements and an aerosol generating device including the light emitting module.

It should be noted that technical objects of the present embodiments are not limited to the above-described technical objects, and other technical objects will be apparent to those skilled in the art from the following embodiments.

Solution to Problem

A light emitting element according to an embodiment includes: a light emitting portion mounted on a PCB and configured to emit light; a light shield portion spaced from the PCB and having an opening that is formed at a location corresponding to the light emitting portion and passes light emitted from the light emitting portion; a sealing portion positioned between the light shield portion and the PCB and configured to prevent light emitted from the light emitting portion from leaking between the light shield portion and the PCB; and a transmission portion contacting one surface of the light shield portion and configured to transmit light, the one surface facing a direction away from the light emitting portion, wherein the opening has an inclined surface that is an outer circumferential surface located at one end of the opening away from the light emitting portion and widened in the direction away from the light emitting portion, to prevent spread of light that passed through the opening.

The light emitting element may further include an adhesive portion positioned between the sealing portion and the PCB and bonding the sealing portion with the PCB.

The transmission portion may include a protrusion accommodated in the opening.

The sealing portion may include an elastic material.

The light shield portion may include a material having a glass transition temperature that is higher than a glass transmission temperature of the transmission portion. An inner wall of the opening of the light shield portion may include a mirror surface having surface roughness of $Ra \leq 1$ to reflect light.

The inclined surface of the opening may be inclined in a direction toward a center of the opening.

The inclined surface of the opening may be curved convexly in a direction toward a center of the opening.

The inclined surface of the opening may be curved concavely in a direction away from a center of the opening.

The inclined surface of the opening may have a variable curvature.

A light emitting module according to another embodiment may include a plurality of light emitting elements.

An aerosol generating device according to another embodiment may include a light emitting module including a plurality of light emitting elements.

A method of manufacturing a light emitting element includes: mounting a light emitting portion emitting light on a PCB; positioning a light shield portion to be spaced from the PCB, the light shield portion having an opening formed at a location corresponding to the light emitting portion and passing light emitted from the light emitting portion; positioning a sealing portion between the light shield portion and the PCB, the sealing portion preventing light emitted from the light emitting portion from leaking between the light shield portion and the PCB; and positioning a transmission portion transmitting light such that the transmission portion contacts one surface of the light shield portion, the one surface facing a direction away from the light emitting portion, wherein the opening has an inclined surface that is an outer circumferential surface located at one end of the opening away from the light emitting portion and widened in the direction away from the light emitting portion, to prevent spread of light that passed through the opening of the light shield portion.

Advantageous Effects of Disclosure

The light emitting element according to an embodiment includes the opening having the inclined surface that is an outer circumferential surface located at one end of the opening and widened in the direction away from the light emitting portion, so that light emitted from the light emitting element may proceed in parallel to the center axis of the opening. Accordingly, spread of light emitted from the light emitting element may be prevented to improve a visual effect of the light emitting element, thereby more clarifying the meaning of a visual signal.

The light emitting module including the plurality of light emitting elements according to the above-described embodiment and the aerosol generating device including the light emitting module are provided according to the current embodiments. Accordingly, the use convenience of a user using electronic equipment including the aerosol generating device may be improved.

BEST MODE

A light emitting element according to an embodiment includes: a light emitting portion mounted on a PCB and configured to emit light; a light shield portion spaced from the PCB and having an opening that is formed at a location corresponding to the light emitting portion and passes light emitted from the light emitting portion; a sealing portion positioned between the light shield portion and the PCB, and configured to prevent light emitted from the light emitting portion from leaking between the light shield portion and the PCB; and a transmission portion contacting one surface of the light shield portion and configured to transmit light, the one surface facing a direction away from the light emitting portion, wherein the opening has an inclined surface that is an outer circumferential surface located at one end of the opening away from the light emitting portion and widened in the direction away from the light emitting portion, to prevent spread of light that passed through the opening.

MODE OF DISCLOSURE

With respect to the terms in the various embodiments, the general terms which are currently and widely used are selected in consideration of functions of structural elements in the various embodiments of the present disclosure. However, meanings of the terms can be changed according to intention, a judicial precedence, the appearance of a new technology, and the like. In addition, in certain cases, a term which is not commonly used can be selected. In such a case, the meaning of the term will be described in detail at the corresponding portion in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Hereinafter, the present disclosure will now be described more fully with reference to the accompanying drawings, in which example embodiments of the present disclosure are shown such that one of ordinary skill in the art may easily work the present disclosure. The disclosure may, however, be embodied in many different forms and should not be construed as being limited to the embodiments set forth herein.

Hereinafter, example embodiments of the present disclosure will be described in detail with reference to the drawings.

Figure 1A:
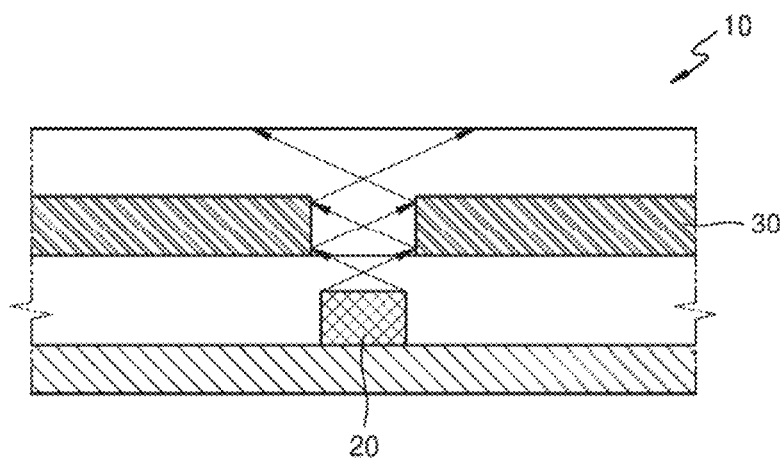
FIG. 1A is a cross-sectional view of a typical light emitting element.

FIG. 1A is a cross-sectional view of a typical light emitting element 10. The typical light emitting element 10 will be described in more detail with reference to FIG. 1A. Referring to FIG. 1A, the typical light emitting element 10 may include a light emitting portion 20 and a light shield portion 30 having an opening formed at a location corresponding to the light emitting portion 20 and passing light emitted from the light emitting portion 20 in one direction.

The opening of the light shield portion 30 of the typical light emitting element 10 may have a constant width. That is, the opening may include an internal cavity having a cylinder shape, and the width of the opening may be constant regardless of distances from the light emitting portion 20.

Referring to FIG. 1A, a path of light passing through the opening formed in the light shield portion 30 of the typical light emitting element 10 will be schematically understood. Light passing through the opening having the constant width may be reflected from an inner wall of the opening and emitted to outside of the typical light emitting element 10. Because the inner wall of the opening may form a flat surface, light reflected from the inner wall of the opening may form, outside the light emitting element 10, an image having a larger area than a cross-section of the opening. Then, the image formed outside the typical light emitting element 10 may be visually recognized by a user.

When an image of an area that is larger than that of the cross-section of the opening is formed outside the light emitting element 10, a light spread phenomenon in which a density of light is reduced and a visual effect deteriorates may occur. Accordingly, a user who uses an electronic device with the typical light emitting element 10 may have difficulties in correctly recognizing a visual mark represented by the light emitting element 10, due to the light spread phenomenon caused by the internal structure of the light emitting element 10.

Figure 1B:
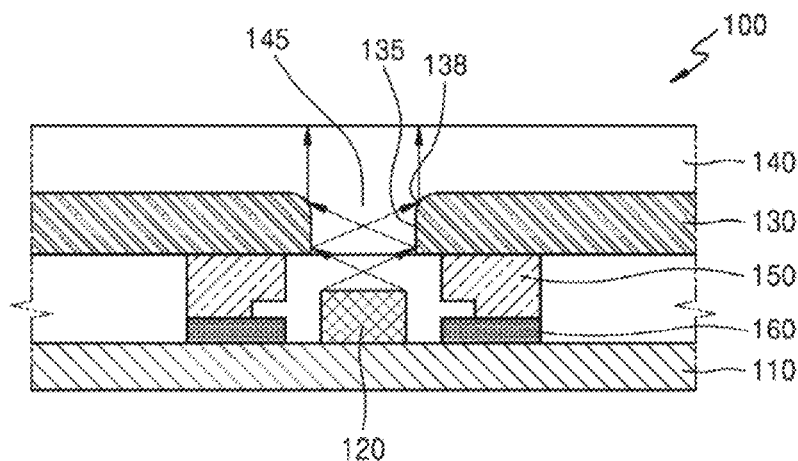
FIG. 1B is a cross-sectional view of a light emitting element according to an embodiment.

FIG. 1B is a cross-sectional view of a light emitting element 100 according to an embodiment. The light emitting element 100 according to an embodiment will be described in more detail with reference to FIG. 1B.

The light emitting element 100 according to the embodiment shown in FIG. 1B may include a light emitting portion 120 mounted on a Printed Circuit Board (PCB) 110 to emit light, a light shield portion 130 spaced from the PCB 110 and having an opening 135 formed at a location corresponding to the light emitting portion 120 and passing light emitted from the light emitting portion 120 in one direction, a sealing portion 150 positioned between the light shield portion 130 and the PCB 110 to prevent light emitted from the light emitting portion 120 from leaking between the light shield portion 130 and the PCB 110, and a transmission portion 140 contacting one surface of the light shield portion 130 toward a direction away from the light emitting portion 120 to transmit light.

In the light emitting element 100 according to an embodiment, the opening 135 of the light shield portion 130 may have an inclined surface 138 that is an outer circumferential surface located at one end of the opening 135 away from the light emitting portion 120. The opening 135 becomes wider in the direction away from the light emitting portion 120, in order to prevent spread of light that passes through the opening 135 of the light shield portion 130.

Also, the light emitting element 100 according to an embodiment may further include an adhesive portion 160 positioned between the sealing portion 150 and the PCB 110, which bonds the sealing portion 150 with the PCB 110.

The light emitting element 100 according to an embodiment may include the PCB 110 and the light emitting portion 120 mounted on the PCB 110 and emitting light, and the light emitting portion 120 may include a light source. The light source of the light emitting portion 120 may be, for example, a light emitting diode (LED), although not limited thereto.

The light emitting element 100 may include the light shield portion 130, and the light shield portion 130 may have the opening 135 formed at the location corresponding to the light emitting portion 120. The light shield portion 130 may cause light emitted from the light emitting portion 120 to proceed toward a direction in which the opening 135 is formed. That is, the light shield portion 130 may prevent light emitted from the light emitting portion 120 from being diverged toward the outside of the opening 135 and enable light to have directivity.

The opening 135 formed at the location corresponding to the light emitting portion 120 may include a cavity formed in the shape of a cylinder. The opening 135 may have the inclined surface 138 that is an outer circumferential surface located at one end of the opening 135 away from the light emitting portion 120 and widened in the direction away from the light emitting portion 120. In other words, a width of the one end of the opening 135 may increase in the direction away from the light emitting portion 120.

The light emitting element 100 may include the sealing portion 150 positioned between the light shield portion 130 and the PCB 110 to prevent light emitted from the light emitting portion 120 from leaking between the light shield portion 130 and the PCB 110. The sealing portion 150 may be formed of an elastic material and compressed between the light shield portion 130 and the PCB 110.

The sealing portion 150 compressed between the light shield portion 130 and the PCB 110 may tightly seal a gap between the light shield portion 130 and the sealing portion 150 and a gap between the sealing portion 150 and the PCB 110. Because light emitted from the light emitting portion 120 is prevented from leaking between the light shield portion 130 and the PCB 110 by the sealing portion 150, the light emitted from the light emitting portion 120 may be emitted to the outside through the opening 135 of the light shield portion 130.

The light emitting element 100 may include the transmission portion 140 contacting one surface of the light shield portion 130, the surface away from the light emitting portion 120, to transmit light emitted through the opening 135 of the light shield portion 130.

The transmission portion 140 may contact the one surface of the light shield portion 130 and be tightly coupled to the light shield portion 130. The transmission portion 140 may be formed of a transparent material capable of transmitting light. Light emitted from the light emitting portion 120 may pass through the opening 135 of the light shield portion 130 and then be transmitted through the transmission portion 140. The light transmitted through the transmission portion 140 may be visually recognized by a user so that the light emitting element 100 may provide a visual effect and stimulus to the user.

The transmission portion 140 may include a protrusion 145 accommodated in the opening 135 of the light shield portion 130. The protrusion 145 extending from one surface of the transmission portion 140 toward the opening 135 of the light shield portion 130 may be accommodated in the opening 135 of the light shield portion 130. The one surface of the transmission portion 140 and the protrusion 145 extending from the one surface of the transmission portion 140 may be in close contact with the light shield portion 130.

Because the protrusion 145 of the transmission portion 140 may be formed of a transparent material capable of transmitting light, light emitted from the light emitting portion 120 may pass through the protrusion 145 of the transmission portion 140 to be reflected from an inner wall of the opening 135 of the light shield portion 130. That is, the transmission portion 140 may protect the light shield portion 130 without changing a path of light emitted from the light emitting portion 120.

The transmission portion 140 may form an outermost surface of the light emitting element 100 to maintain and protect an internal structure of the light emitting element 100. Accordingly, light that is emitted from the light emitting portion 120 and reflected from the inner wall of the opening 135 of the light shield portion 130 and then passes through the transmission portion 140 may be recognized by the user.

The light emitting element 100 may further include the adhesive portion 160 positioned between the sealing portion 150 and the PCB 110, which bonds the sealing portion 150 with the PCB 110.

An adhesive may be applied on both surfaces of the adhesive portion 160, and the adhesive portion 160 may be positioned between the sealing portion 150 and the PCB 110. The adhesive portion 160 positioned between the sealing portion 150 and the PCB 110 may bond the sealing portion 150 with the PCB 110 so as to fix the sealing portion 150 to the PCB 110.

Referring to FIG. 1B, a path of light passing through the opening 135 formed in the light shield portion 130 of the light emitting element 100 will be schematically understood.

The light emitting element 100 according to an embodiment may include the light emitting portion 120 including an LED. The light emitting portion 120 may be electrically connected to the PCB 110 to emit light. The light emitting portion 120 of the light emitting element 100 may select one color from among a plurality of colors to emit light. Accordingly, light emitted by the light emitting element 100 may depend on a color of light emitted from the light emitting portion 120 of the light emitting element 100. Light emitted from the light emitting portion 120 may pass through the opening 135 formed in the light shield portion 130.

The sealing portion 150 may be positioned between the light shield portion 130 and the PCB 110. Because the sealing portion 150 may be formed of an elastic material, the sealing portion 150 may be compressed between the light shield portion 130 and the PCB 110 to tightly seal a gap between the light shield portion 130 and the PCB 110. The sealing portion 150 may adhere and be fixed to the PCB 110 through the adhesive portion 160 of which both surfaces an adhesive is applied on. Accordingly, the sealing portion 150 positioned between the light shield portion 130 and the PCB 110 may prevent light from leaking between the light shield portion 130 and the PCB 110.

The opening 135 of the light shield portion 130 may have the inclined surface 138 that is an outer circumferential surface located at one end of the opening 135, which is an end away from the light emitting portion 120. The opening 135 may become wider in the direction away from the light emitting portion 120. The inclined surface 138 of the opening 135 may have a predetermined inclination.

Light may be reflected from a flat surface of the opening 135, then be reflected from the inclined surface 138 formed at one end of the opening 135, which is an end away from the light emitting portion 120, and proceed toward the transmission portion 140. The inclined surface 138 may have a predetermined inclination toward a center of the opening 135. Light reflected from the inclined surface 138 may have a light path that is different from that of light reflected from the flat surface.

Light reflected from the inclined surface 138 of the opening 135 may proceed in a direction that is parallel to a center axis of the opening 135. Accordingly, light reflected from the inclined surface 138 of the opening 135 and proceeding in the direction that is parallel to the center axis of the opening 135 may have a light path that is different from a path of light reflected from the flat inner wall of the opening 135 and passing the center axis of the opening 135.

Light passing through the opening 135 of the light emitting element 100 and transmitted through the transmission portion 140 may form an image having an area that is similar to an area of a cross-section of the opening 135, on one surface of the transmission portion 140. The image formed on the one surface of the transmission portion 140 may be visually recognized by a user.

Light emitted from the general light emitting element 10 may pass the center axis of the opening 135 and proceed in a radial direction to form an image over a wider area than the opening 135, which may cause light spread. Unlike this, because the light emitting element 100 according to an embodiment includes the opening 135 having the inclined surface 138 at one end away from the light emitting portion 120, light emitted from the light emitting element 100 may proceed in parallel to the center axis of the opening 135.

An area of an image formed by light that passed through the opening 135 of the light shield portion 130 may be similar to an area of a cross-section of the opening 135. Light that exited the light shield portion 130 of the light emitting element 100 according to an embodiment may proceed in parallel to the center axis of the opening 135 to prevent light spread, thereby improving a visual effect of the light emitting element 100.

Figure 2:
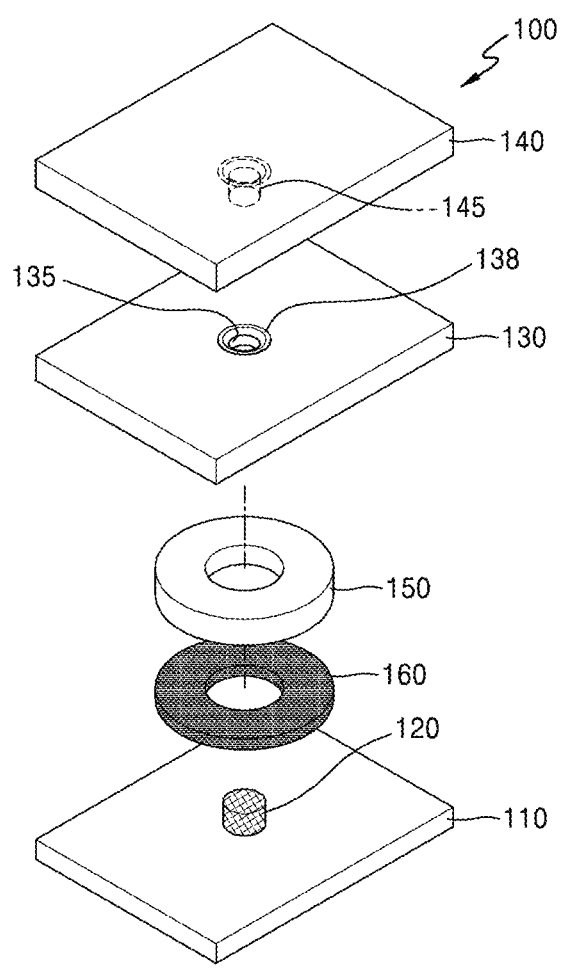
FIG. 2 is an exploded perspective view of the light emitting element according to the embodiment shown in FIG. 1B.

FIG. 2 is an exploded perspective view of the light emitting element 100 according to the embodiment shown in FIG. 1B.

A shape, arrangement, and coupling relationship of an internal structure of the light emitting element 100 according to an embodiment will be described in more detail with reference to FIG. 2.

The light emitting element 100 according to an embodiment may include the PCB 110 and the light emitting portion 120 that may be mounted on the PCB 110. The light emitting portion 120 may be electrically connected to the PCB 110 to receive power from the PCB 110 and emit light.

The light emitting element 100 according to an embodiment may include the light shield portion 130, and the light shield portion 130 may have the opening 135 formed at the location corresponding to the light emitting portion 120 and passing light emitted from the light emitting portion 120 in one direction. The opening 135 may include an internal cavity having a cylinder shape.

The inner wall of the opening 135 of the light shield portion 130 may form a mirror surface having surface roughness of Ra≤1 to reflect light. That is, the inner wall of the opening 135 of the light shield portion 130 may reflect light emitted from the light emitting portion 120 without absorbing the light to cause the light to proceed to the inside of the opening 135 of the light shield portion 130.

The light shield portion 130 may be, for example, formed of a synthetic resin having formability. In this case, the light shield portion 130 may further include a material for opacifying the light shield portion 130. Accordingly, the light shield portion 130 may have a black color of low brightness, although not limited thereto.

Because the light shield portion 130 may further include a material for opacifying the light shield portion 130, light proceeding toward the main body of the light shield portion 130 instead of the inside of the opening 135 of the light shield portion 130 may be absorbed by the light shield portion 130. Accordingly, the light shield portion 130 may emit light emitted from the light emitting portion 120 and simultaneously cause light emitted from the light emitting portion 120 through the opening 135 formed in the light shield portion 130 to proceed in a direction in which the opening 135 extends.

The light emitting element 100 may include the sealing portion 150 positioned between the light shield portion 130 and the PCB 110. The sealing portion 150 may surround the light emitting portion 120. Because the sealing portion 150 surrounds the light emitting portion 120 and is positioned between the light shield portion 130 and the PCB 110, light emitted from the light emitting portion 120 may be prevented from leaking between the light shield portion 130 and the PCB 110.

The sealing portion 150 may include an elastic material, and the elastic material may be a material, such as, for example, rubber, plastic having elasticity, sponge, etc., although not limited thereto. The sealing portion 150 is not limited as long as it is formed of a material capable of blocking light. The sealing portion 150 may be positioned between the light shield portion 130 and the PCB 110 and compressed by the light shield portion 130 and the PCB 110. Accordingly, the sealing portion 150 may tightly seal a space between the light shield portion 130 and the PCB 110 to prevent light from leaking between the light shield portion 130 and the PCB 110.

The sealing portion 150 may be bonded with the PCB 110 through the adhesive portion 160 positioned between the sealing portion 150 and the PCB 110. The adhesive portion 160 may fix the sealing portion 150 to the PCB 110, and surround the light emitting portion 120 to prevent light emitted from the light emitting portion 120 from leaking between the sealing portion 150 and the PCB 110.

An adhesive may be applied on both surfaces of the adhesive portion 160 to bond the sealing portion 150 with the PCB 110, and the adhesive portion 160 may be formed of an opaque material. The adhesive portion 160 may have a black color of low brightness, although not limited thereto.

The adhesive portion 160 may include an elastic material, and be positioned between the sealing portion 150 and the PCB 110 to form a light shielding structure together with the sealing portion 150.

The transmission portion 140 of the light emitting element 100 according to an embodiment may contact one surface of the light shield portion 130, which is a surface away from the light emitting portion 120. The transmission portion 140 may be in close contact with the one surface of the light shield portion 130 to prevent light from leaking between the transmission portion 140 and the light shield portion 130.

For the transmission portion 140 to be in close contact with one surface of the light shield portion 130 to seal the space between the transmission portion 140 and the light shield portion 130, the transmission portion 140 may be formed on the light shield portion 130 by an insert-injection method. In this case, the transmission portion 140 may include a material capable of being fused with the light shield portion 130, and a glass transition temperature of the light shield portion 130 may be higher than that of the transmission portion 140.

After the light shield portion 130 is first manufactured and then cooled, the transmission portion 140 may be coupled to the light shield portion 130 by the insert-injection method. Because the glass transition temperature of the light shield portion 130 is higher than that of the transmission portion 140, the transmission portion 140 may maintain its shape without being deformed when the transmission portion 140 is formed on the light shield portion 130 by the insert-injection method. Therefore, one surface of the light shield portion 130 and the inner wall of the opening 135, contacting the transmission portion 140 may be not deformed.

Because the shape of the inner wall of the opening 135 of the light shield portion 130 is maintained, the inner wall of the opening 135 of the light shield portion 130 may form a mirror surface having surface roughness of Ra≤1 to reflect light.

The transmission portion 140 may be formed of a synthetic resin having formability and high permeability to transmit light that passed through the opening 135 of the light shield portion 130. More specifically, the transmission portion 140 may be transparent to transmit light that passed through the opening 135 of the light shield portion 130. Because the transmission portion 140 is transparent, light that passed through the opening 135 of the light shield portion 130 may be transmitted through the transmission portion 140 and then recognized by a user. Through the light recognized by the user, the light emitting element 100 may provide a visual effect and mark to the user.

The transmission portion 140 may include the protrusion 145 accommodated in the opening 135 of the light shield portion 130 and contacting the inner wall of the opening 135. The protrusion 145 of the transmission portion 140 may be in close contact with the inner wall of the opening 135 of the light shield portion 130 to seal the space between the transmission portion 140 and the light shield portion 130.

Light emitted from the light emitting portion 120 may pass through the protrusion 145 of the transmission portion 140 and be reflected from the inner wall of the opening 135 of the light shield portion 130. The light reflected from the inner wall of the opening 135 may be transmitted through the transmission portion 140.

Figure 3A:
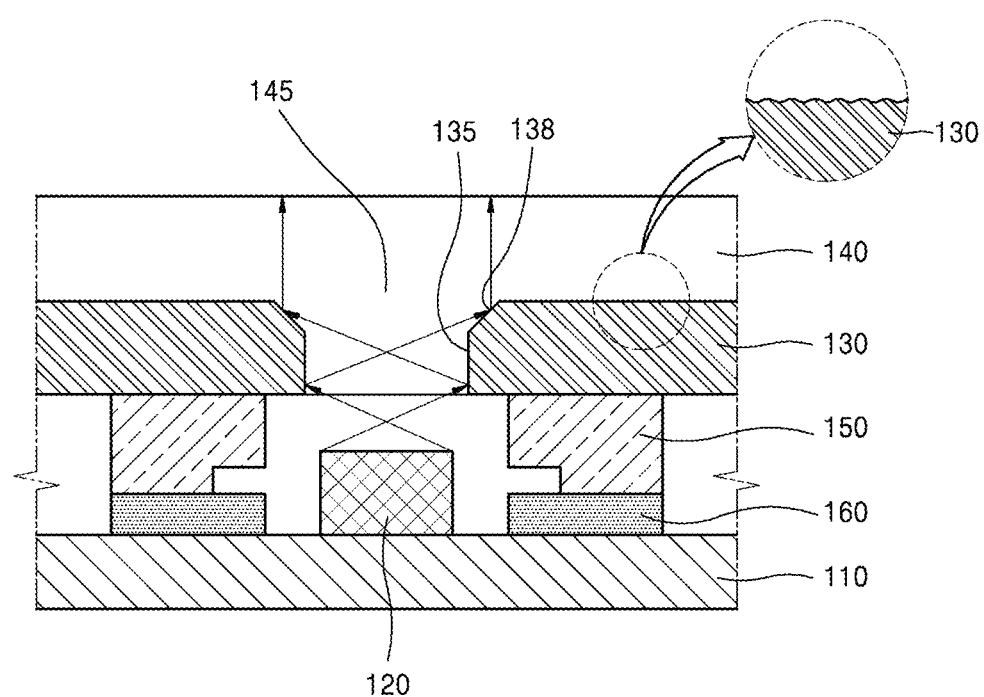
FIGS. 3A to 3C are cross-sectional views showing example shapes of a light shield portion of a light emitting element according to another embodiment.
Figure 3B:
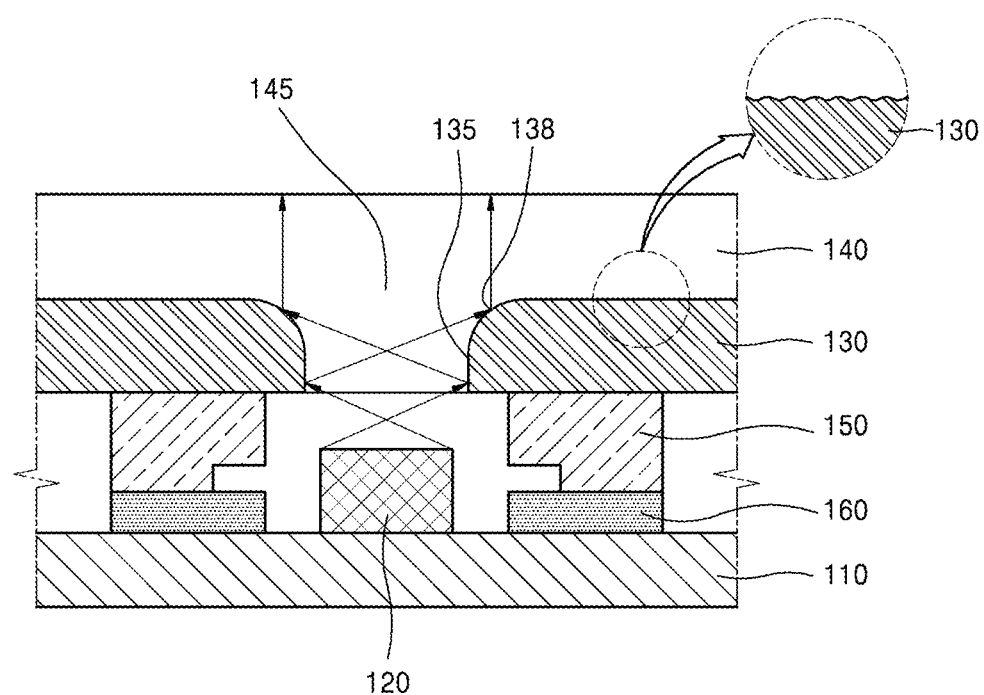
Figure 3C:
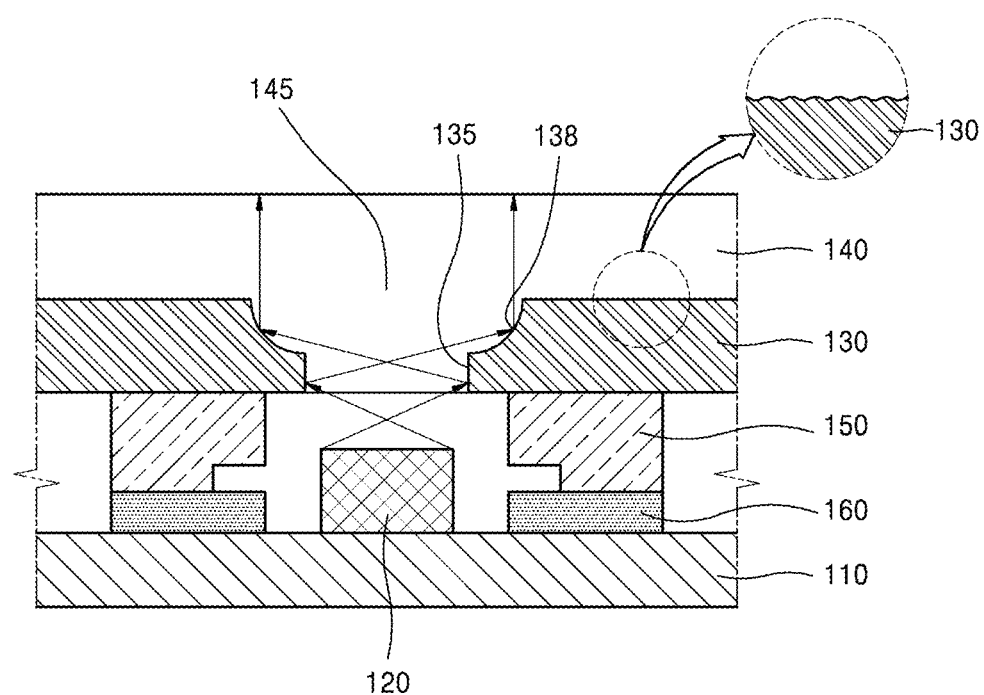

FIGS. 3A to 3C are cross-sectional views showing example shapes of the light shield portion 130 of the light emitting element 100 according to another embodiment.

The light shield portion 130 may include the opening 135 formed at the location corresponding to the light emitting portion 120. The opening 135 of the light shield portion 130 may include a cavity having a cylinder shape. The opening 135 may have the inclined surface 138 that is an outer circumferential surface located at one end of the opening 135, which is an end away from the light emitting portion 120, and widened in the direction away from the light emitting portion 120. That is, a width of the one end of the opening 135 may increase in the direction away from the light emitting portion 120.

Referring to FIG. 3A, an example shape of the inclined surface 138 of the opening 135 is shown. The inclined surface 138 of the opening 135 formed at one end away from the light emitting portion 120 may be inclined toward a center of the opening 135. That is, the outer circumferential surface of the opening 135 may become wider or narrower in the direction away from the light emitting portion 120, and an inclination of the widening or narrowing outer circumferential surface may be constant.

The inner wall of the opening 135 may include the inclined surface 138 inclined downward toward the center of the opening 135. The inner wall of the opening 135 may form a mirror surface having surface roughness of Ra≤1 to reflect light. That is, light emitted from the light emitting portion 120 may be reflected from the inner wall of the opening 135 to pass a center axis of the inner wall of the opening 135. Light reflected from the inclined surface 138 of the opening 135 may proceed in parallel to the center axis of the opening 135.

Light reflected from the inclined surface 138 inclined downward toward the center of the opening 135 may be transmitted through the transmission portion 140 to form an image having an area that is similar to an area of a cross-section of the opening 135 on one surface of the transmission portion 140. The image formed on the one surface of the transmission portion 140 may be visually recognized by a user. The protrusion 145 of the transmission portion 140 may be in close contact with the opening 135 of the light shield portion 130, and light reflected from the inner wall of the opening 135 may be transmitted through the transmission portion 140 and proceed.

A surface of a main body of the light shield portion 130, that is, a surface of the light shield portion 130 except for the inner wall of the opening 135 of the light shield portion 130, may have greater roughness than that of the inner wall of the opening 135 of the light shield portion 130. That is, the surface of the main body of the light shield portion 130 may be rougher than the inner wall of the opening 135 of the light shield portion 130.

As described above, if the light shield portion 130 includes an opaque material and the roughness of the main body of the light shield portion 130 is rougher than that of the inner wall of the opening 135 of the light shield portion 130, light proceeding toward the main body of the light shield portion 130 instead of the inside of the opening 135 of the light shield portion 130 may be absorbed by the light shield portion 130.

Accordingly, the light shield portion 130 may block light emitted from the light emitting portion 120 and proceeding toward the main body of the light shield portion 130. Also, the light shield portion 130 may cause light emitted from the light emitting portion 120 toward the opening 135 of the light shield portion 130 formed at one end of the light shield portion 130 to proceed in a predetermined direction.

Referring to FIG. 3B, another example shape of the inclined surface 138 of the opening 135 is shown. The inclined surface 138 of the opening 135 formed at one end of the light shield portion 130 may be curved convexly in a direction toward the center of the opening 135. That is, the inclined surface 138 of the opening 135 may widen at a greater rate away from the light emitting portion 120.

The inner wall of the opening 135 may include the inclined surface 138 curved convexly in the direction toward the center of the opening 135. The inner wall of the opening 135 may form a mirror surface having surface roughness of Ra≤1 to reflect light. That is, light emitted from the light emitting portion 120 may be reflected from the inner wall of the opening 135, and pass the center axis of the inner wall of the opening 135 to arrive at the inclined surface 238 of the opening 135. Light reflected from the inclined surface 138 of the opening 135 may proceed in parallel to the center axis of the opening 135.

Light reflected from the inclined surface 138 curved convexly toward the center of the opening 135 may be transmitted through the transmission portion 140 to form an image having an area that is similar to an area of a cross-section of the opening 135 on one surface of the transmission portion 140. The image formed on the one surface of the transmission portion 140 may be visually recognized by a user.

The surface of the main body of the light shield portion 130, that is, the surface of the light shield portion 130 excluding the inner wall of the opening 135 of the light shield portion 130, may have greater roughness than that of the inner wall of the opening 135 of the light shield portion 130. That is, the surface of the main body of the light shield portion 130 may be rougher than the inner wall of the opening 135 of the light shield portion 130.

Because the main body of the light shield portion 130 has a rough surface, light emitted toward the main body of the light shield portion 130 may be easily absorbed by the light shield portion 130. Accordingly, the light shield portion 130 may absorb light emitted toward the main body of the light shield portion 130 among light emitted from the light emitting portion 120, and transmit light emitted toward the opening 135 of the light shield portion 130 among the light emitted from the light emitting portion 120.

Accordingly, the light shield portion 130 may block light emitted from the light emitting portion 120 and proceeding toward the main body of the light shield portion 130. Also, the light shield portion 130 may cause light emitted toward the opening of the light shield portion 130 from the light emitting portion 120 to proceed in a predetermined direction.

Referring to FIG. 3C, still another example shape of the inclined surface 138 of the opening 135 is shown. The inclined surface 138 of the opening 135 formed at one end of the light shield portion 130 may be curved concavely in a direction away from the center of the center 135. That is, the inclined surface 138 of the opening 135 may widen at a smaller rate in the direction away from the light emitting portion 120.

The inner wall of the opening 135 may include the inclined surface 138 curved concavely in the direction away from the center of the opening 135. As described above, the inner wall of the opening 135 may form a mirror surface having surface roughness of Ra≤1 to reflect light. That is, light emitted from the light emitting portion 120 may be reflected from the inner wall of the opening 135, and pass the center axis of the inner wall of the opening 135 to arrive at the inclined surface 138 of the opening 135. Light reflected from the inclined surface 138 of the opening 135 may proceed in parallel to the center axis of the opening 135.

The surface of the main body of the light shield portion 130 may have greater roughness than that of the inner wall of the opening 135 of the light shield portion 130. That is, the surface of the main body of the light shield portion 130 may be rougher than the inner wall of the opening 135 of the light shield portion 130.

Because the main body of the light shield portion 130 has a rough surface, light proceeding toward the main body of the light shield portion 130 may be easily absorbed by the light shield portion 130. Accordingly, the light shield portion 130 may absorb light proceeding toward the main body of the light shield portion 130 among light emitted from the light emitting portion 120, and transmit light toward the opening 135 of the light shield portion 130 among the light emitted from the light emitting portion 120.

Accordingly, the light shield portion 130 may block light emitted from the light emitting portion 120 and proceeding toward the main body of the light shield portion 130. Also, the light shield portion 130 may cause light emitted toward the opening 135 of the light shield portion 130 from the light emitting portion 120 to proceed in a predetermined direction, that is, in a direction that is substantially parallel to a direction in which the opening 135 extends.

As shown in FIG. 3B, the inclined surface 138 of the opening 135 formed at one end of the light shield portion 130 may be curved convexly in the direction toward the center of the opening 135. Also, as shown in FIG. 3C, the inclined surface 138 of the opening 135 formed at one end of the light shield portion 130 may be curved concavely in the direction away from the center of the opening 135.

When the inclined surface 138 of the opening 135 is curved to form a convexly or concavely curved surface, the inclined surface 138 of the opening 135 may have a constant curvature. That is, a rate at which an inclination of the inclined surface 138 of the opening 135 increases or decreases may be constant.

Alternatively, the inclined surface 138 of the opening 135 may have a variable curvature. That is, a rate at which the inclination of the inclined surface 138 increases or decreases may depend on a distance from the light emitting portion 120, and the inclination of the inclined surface 138 may be within a predetermined range. Because the inclined surface 138 of the opening 135 may have a variable curvature, a path of light reflected from the inclined surface of the opening 135 may be adjusted.

Figure 4:
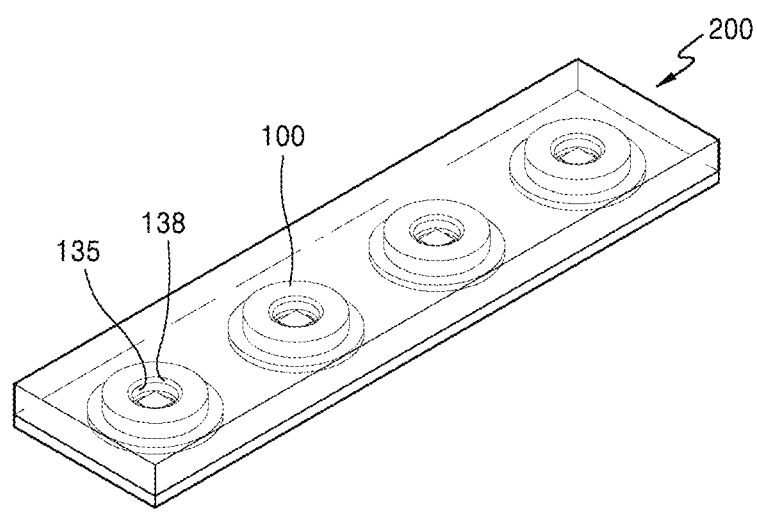
FIG. 4 is a perspective view of a light emitting module including a plurality of light emitting elements, each of which is the light emitting element according to the embodiments shown in FIGS. 1B to 3C.

FIG. 4 is a perspective view of a light emitting module 200 including a plurality of light emitting elements 100, each of which is the light emitting element 100 according to the embodiments shown in FIGS. 1B to 3C.

The light emitting module 200 may include a plurality of light emitting elements 100. In this case, the light emitting elements 100 may be arranged in parallel inside the light emitting module 200 and selectively operate inside the light emitting module 200.

Each of the plurality of light emitting elements 100 included in the light emitting module 200 may include the PCB 110, the light emitting portion 120 mounted on the PCB 110 to emit light, the light shield portion 130 spaced from the PCB 110 and having the opening 135 formed at the location corresponding to the light emitting portion 120 and passing light emitted from the light emitting portion 120 in one direction, the sealing portion 150 positioned between the light shield portion 130 and the PCB 110 to prevent light emitted from the light emitting portion 120 from leaking between the light shield portion 130 and the PCB 110, and the transmission portion 140 contacting one surface of the light shield portion 130, which is a surface away from the light emitting portion 120, to transmit light. The opening 135 of the light emitting portion 120 may include the inclined surface 138 that is an outer circumferential surface located at one end of the opening 135, which is an end away from the light emitting portion 120. The inclined surface 138 may be widened in the direction away from the light emitting portion 120, in order to prevent spread of light that passed through the opening 135 of the light shield portion 130.

The light emitting elements 100 included in the light emitting module 200 have been described above with regard to the light emitting element 100 of the above-described embodiment, and, therefore, repeated descriptions thereof will be omitted.

The plurality of light emitting elements 100 included in the light emitting module 200 may selectively emit different colors, respectively. Accordingly, the light emitting module 200 may combine colors emitted from the light emitting elements 100 to provide different visual signals.

The plurality of light emitting elements 100 included in the light emitting module 200 may selectively emit different colors, and also be selectively turned on/off according to electrical signals. Therefore, by independently turning on/off the light emitting elements 100 and combining turning-on/off operations of the light emitting elements 100, different visual signals may be provided to the user.

Figure 5A:
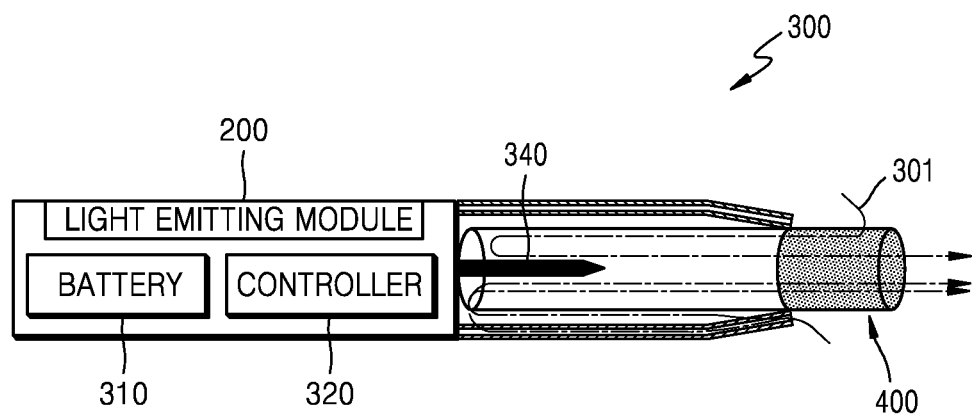
FIGS. 5A and 5B are block diagrams schematically showing an aerosol generating device according to another embodiment including the light emitting module shown in FIG. 4.
Figure 5B:
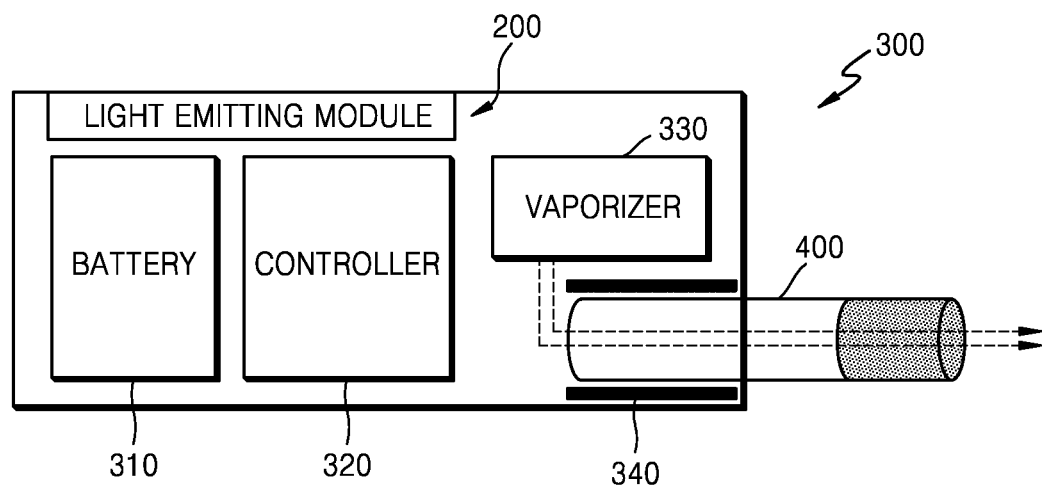
Figure 5C:
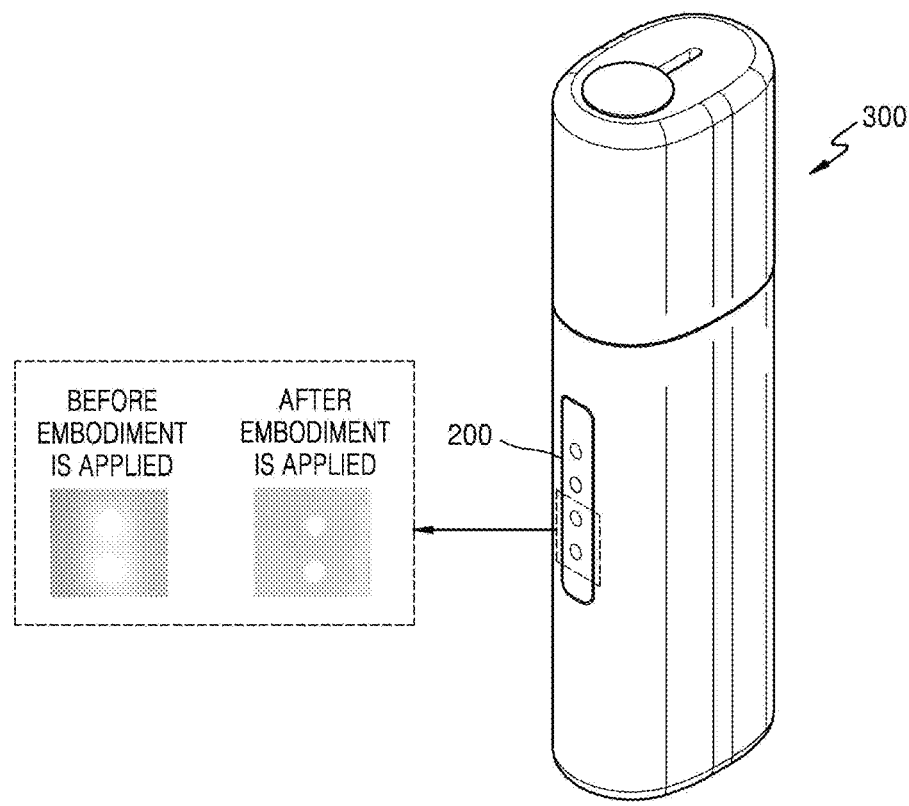
FIG. 5C is a perspective view of the aerosol generating device shown in FIGS. 5A and 5B.

FIGS. 5A and 5B are block diagrams schematically showing an aerosol generating device 300 according to another embodiment including the light emitting module 200 shown in FIG. 4, and FIG. 5C is a perspective view of the aerosol generating device 300 including the light emitting module 200 shown in FIGS. 5A and 5B.

Referring to FIG. 5A, the aerosol generating device 300 may include a battery 310, a controller 320, and a heater 340. In FIG. 5A, the battery 310, the controller 320, and the heater 340 are shown to be arranged in a line.

Referring to FIG. 5B, the aerosol generating device 300 may include the battery 310, the controller 320, the heater 340, a vaporizer 330, and the light emitting module 200. Also, a cigarette 400 may be inserted into an inside space of the aerosol generating device 300. According to a design of the aerosol generating device 300, an arrangement of the battery 310, the controller 320, the heater 340, and the vaporizer 330 may change.

FIGS. 5A and 5B illustrate components of the aerosol generating device 300, which are related to the present embodiment. Therefore, it will be understood by one of ordinary skill in the art related to the present embodiment that other general-purpose components may be further included in the aerosol generating device 300, in addition to the components illustrated in FIGS. 5A and 5B Also, FIGS. 5A and 5B illustrate that the aerosol generating device 300 includes the heater 340. However, as necessary, the heater 340 may be omitted.

When the cigarette 400 is inserted into the aerosol generating device 300, the aerosol generating device 300 may operate the heater 340 and/or the vaporizer 330 to generate aerosol from the cigarette 400 and/or the vaporizer 330. The aerosol generated by the heater 340 and/or the vaporizer 330 is delivered to a user by passing through the cigarette 400. According to an embodiment, even when the cigarette 400 is not inserted into the aerosol generating device 300, the aerosol generating device 300 may heat the heater 340.

The battery 310 may supply power to be used for the aerosol generating device 300 to operate. For example, the battery 310 may supply power to heat the heater 340 or the vaporizer 330, and may supply power for operating the controller 320. Also, the battery 310 may supply power for operations of a display, a sensor, a motor, etc. mounted in the aerosol generating device 300.

The controller 320 may generally control operations of the aerosol generating device 300. In detail, the controller 320 may control not only operations of the battery 310, the heater 340, and the vaporizer 330, but also operations of other components included in the aerosol generating device 300. Also, the controller 320 may check a state of each of the components of the aerosol generating device 300 to determine whether or not the aerosol generating device 300 is able to operate.

The controller 320 may include at least one processor. A processor can be implemented as an array of a plurality of logic gates or can be implemented as a combination of a general-purpose microprocessor and a memory in which a program executable in the microprocessor is stored. It will be understood by one of ordinary skill in the art that the processor can be implemented in other forms of hardware.

The light emitting module 200 may be positioned inside the aerosol generating device 300 to emit light to the outside of the aerosol generating device 300. Through light emitted from the light emitting module 200, the aerosol generating device 300 may provide a visual mark to a user.

The light emitting module 200 may include the plurality of light emitting elements 100, and the plurality of light emitting elements 100 included in the light emitting module 200 may selectively emit different colors. Accordingly, the aerosol generating device 300 may combine colors emitted from the plurality of light emitting elements 100 to provide different visual signals to a user.

Also, the plurality of light emitting elements 100 of the light emitting module 200 may be selectively turned on/off according to an electrical signal from the controller 320. Accordingly, by independently turning on/off the light emitting elements 100 and combining turning-on/off operations of the light emitting elements 100, different visual signals may be provided to the user.

Visual signals according to colors emitted from the light emitting elements 100 and turning on/off of the light emitting elements 100 may be controlled by the controller 320 of the aerosol generating device 300. Each visual signal according to a color emitted from the light emitting elements 100 of the light emitting module 200 and a turning-on/off combination of the light emitting elements 100 may indicate a state or availability of the aerosol generating device 300.

Accordingly, the user may determine a state and availability of the aerosol generating device 300 based on a visual signal according to a color of light emitted from the light emitting module 200 of the aerosol generating device 300 and a turning-on/turning-off combination of the light emitting module 200.

The heater 340 may be heated by the power supplied from the battery 310. For example, when the cigarette 400 is inserted into the aerosol generating device 300, the heater 340 may be located outside the cigarette 400. Thus, the heated heater 340 may increase a temperature of an aerosol generating material in the cigarette 400.

The heater 340 may include an electro-resistive heater. For example, the heater 340 may include an electrically conductive track, and the heater 340 may be heated when currents flow through the electrically conductive track. However, the heater 340 is not limited to the example described above and may include all heaters which may be heated to a desired temperature. Here, the desired temperature may be pre-set in the aerosol generating device 300 or may be set as a temperature desired by a user.

As another example, the heater 340 may include an induction heater. In detail, the heater 340 may include an electrically conductive coil for heating a cigarette in an induction heating method, and the cigarette may include a susceptor which may be heated by the induction heater.

For example, the heater 340 may include a tube-type heating element, a plate-type heating element, a needle-type heating element, or a rod-type heating element, and may heat the inside or the outside of the cigarette 400, according to the shape of the heating element.

Also, the aerosol generating device 300 may include a plurality of heaters 340. Here, the plurality of heaters 340 may be inserted into the cigarette 400 or may be arranged outside the cigarette 400. Also, some of the plurality of heaters 340 may be inserted into the cigarette 400 and the others may be arranged outside the cigarette 400. In addition, the shape of the heater 340 is not limited to the shapes illustrated in FIGS. 5A and 5B and may include various shapes.

The vaporizer 330 may generate aerosol by heating a liquid composition and the generated aerosol may pass through the cigarette 400 to be delivered to a user. In other words, the aerosol generated via the vaporizer 330 may move along an air flow passage of the aerosol generating device 300 and the air flow passage may be configured such that the aerosol generated via the vaporizer 330 passes through the cigarette 400 to be delivered to the user.

For example, the vaporizer 330 may include a liquid storage, a liquid delivery element, and a heating element, but it is not limited thereto. For example, the liquid storage, the liquid delivery element, and the heating element may be included in the aerosol generating device 300 as independent modules.

The liquid storage may store a liquid composition. For example, the liquid composition may be a liquid including a tobacco-containing material having a volatile tobacco flavor component, or a liquid including a non-tobacco material. The liquid storage may be formed to be detachable from the vaporizer 330 or may be formed integrally with the vaporizer 330.

The liquid delivery element may deliver the liquid composition of the liquid storage to the heating element. For example, the liquid delivery element may be a wick such as cotton fiber, ceramic fiber, glass fiber, or porous ceramic, but is not limited thereto.

For example, the vaporizer 330 may be referred to as a cartomizer or an atomizer, but it is not limited thereto.

The aerosol generating device 300 may further include general-purpose components in addition to the battery 310, the controller 320, the heater 340, and the vaporizer 330. For example, the aerosol generating device 300 may include a display capable of outputting visual information and/or a motor for outputting haptic information. Also, the aerosol generating device 300 may include at least one sensor (a puff detecting sensor, a temperature detecting sensor, a cigarette insertion detecting sensor, etc.). Also, the aerosol generating device 300 may be formed as a structure where, even when the cigarette 400 is inserted into the aerosol generating device 300, external air 301 may be introduced or internal air may be discharged.

The light emitting element 100 according to an embodiment of may include the opening 135 having the inclined surface 138. The inclined surface 138 may be an outer circumferential surface located at one end of the opening 135 and widened in the direction away from the light emitting portion 120 such that light emitted from the light emitting element 100 may proceed in parallel to the center axis of the opening 135. Accordingly, the spread of light emitted from the light emitting element 100 may be prevented and a visual effect of the light emitting element 100 is improved, thereby more clarifying the meaning of a visual signal.

The light emitting module 200 including the plurality of light emitting elements 100, each of which is the light emitting element 100 according to the above-described embodiments, and the aerosol generating device 300 including the light emitting module 200 may be provided according to the embodiments. Accordingly, the use convenience of a user using electronic equipment including the aerosol generating device 300 may be improved.

A method of manufacturing the light emitting element 100, according to an embodiment, may include: mounting the light emitting portion 120 emitting light on the PCB 110; positioning the light shield portion 130 to be spaced from the PCB 110, the light shield portion 130 having the opening 135 formed at a location corresponding to the light emitting portion 120 and passing light emitted from the light emitting portion 120; positioning the sealing portion 150 between the light shield portion 130 and the PCB 110 and configured to prevent light emitted from the light emitting portion 120 from leaking between the light shield portion 130 and the PCB 110; and positioning the transmission portion 140 transmitting light such that the transmission portion 140 contacts one surface of the light shield portion 130 toward a direction away from the light emitting portion 120, wherein the opening 135 has the inclined surface 138 that is an outer circumferential surface located at one end of the opening 135 in the direction away from the light emitting portion 120 and widened in the direction away from the light emitting portion 120, to prevent spread of light that passed through the opening 135 of the light shield portion 130.

A configuration and effect of the method of manufacturing the light emitting element 100 according to an embodiment have been described above with regard to the light emitting element 100, and therefore, repeated descriptions thereof will be omitted.

It will be understood by those of ordinary skill in the art that various changes in form and details may be made therein without departing from the spirit and scope of the above descriptions. Thus, the disclosed methods should be considered in descriptive sense only and not for purposes of limitation. Therefore, the scope of the disclosure is defined not by the detailed description of the disclosure but by the appended claims, and all differences within the scope will be construed as being included in the disclosure.

What is claimed is:

1. A light emitting element comprising: a light emitting portion mounted on a printed circuit board (PCB) and configured to emit light; a light shield portion that is a single element spaced from the PCB and having an opening that is formed at a location corresponding to the light emitting portion and passes light emitted from the light emitting portion; a sealing portion positioned between the light shield portion and the PCB and configured to prevent light emitted from the light emitting portion from leaking between the light shield portion and the PCB; and a transmission portion contacting one surface of the light shield portion and configured to transmit light, the one surface facing a direction away from the light emitting portion, wherein the opening includes a first portion having a uniform diameter and a second portion at a top edge corner of the light shield portion having a varying diameter that becomes wider along the direction away from the light emitting portion such that light emitted from the light emitting portion is reflected on the first portion and then reflected on the second portion.

2. The light emitting element of claim 1, further comprising an adhesive portion positioned between the sealing portion and the PCB and configured to bond the sealing portion with the PCB.

3. The light emitting element of claim 1, wherein the transmission portion comprises a protrusion accommodated in the opening.

4. The light emitting element of claim 1, wherein the sealing portion includes an elastic material.

5. The light emitting element of claim 1, wherein the light shield portion includes a material having a glass transition temperature that is higher than a glass transition temperature of the transmission portion.

6. The light emitting element of claim 1, wherein an inner wall of the opening of the light shield portion includes a mirror surface having surface roughness of Ra≤1 to reflect light.

7. The light emitting element of claim 1, wherein a surface of the second portion is inclined in a direction toward a center of the opening.

8. The light emitting element of claim 1, wherein a surface of the second portion is curved convexly in a direction toward a center of the opening.

9. The light emitting element of claim 1, wherein a surface of the second portion is curved concavely in a direction away from a center of the opening.

10. The light emitting element of claim 1, wherein a surface of the second portion has a variable curvature.

11. A light emitting module comprising a plurality of light emitting elements, each of which is the light emitting element according to claim 1.

12. An aerosol generating device comprising the light emitting module according to claim 11.

13. A method of manufacturing a light emitting element, the method comprising: mounting a light emitting portion emitting light on a printed circuit board (PCB); positioning a light shield portion to be a single element spaced from the PCB, the light shield portion having an opening formed at a location corresponding to the light emitting portion and configured to pass light emitted from the light emitting portion; positioning a sealing portion between the light shield portion and the PCB, the sealing portion preventing light emitted from the light emitting portion from leaking between the light shield portion and the PCB; and positioning a transmission portion transmitting light to contact one surface of the light shield portion, the one surface facing a direction away from the light emitting portion, wherein the opening includes a first portion having a uniform diameter and a second portion at a top edge corner of the light shield portion having a varying diameter that becomes wider along the direction away from the light emitting portion such that light emitted from the light emitting portion is reflected on the first portion and then reflected on the second portion.

* * * * *